United States Patent [19]

White

[11] Patent Number: 5,735,891
[45] Date of Patent: Apr. 7, 1998

[54] SELF-CLAMPING ANCHORING SLEEVE

[75] Inventor: Mark A. White, Friendswood, Tex.

[73] Assignee: Sulzer Intermedics Inc., Angleton, Tex.

[21] Appl. No.: 753,826

[22] Filed: Dec. 2, 1996

[51] Int. Cl.$^6$ .................................. A61N 1/05
[52] U.S. Cl. ............................ 607/126; 606/139
[58] Field of Search .................... 607/116, 118, 607/119, 126, 127, 130, 131; 606/152, 158, 129, 159, 139, 140; 604/175

[56] References Cited

U.S. PATENT DOCUMENTS

| | | | |
|---|---|---|---|
| 4,516,584 | 5/1985 | Garcia | 128/785 |
| 4,820,298 | 4/1989 | Leveen et al. | 623/1 |
| 5,108,417 | 4/1992 | Sawyer | 606/198 |
| 5,129,405 | 7/1992 | Milijasevic et al. | 128/785 |
| 5,273,053 | 12/1993 | Pohndorf | 607/132 |

FOREIGN PATENT DOCUMENTS

PCT/US92/08463  10/1992  WIPO .................. A61F 2/06

*Primary Examiner*—Marvin M. Lateef
*Assistant Examiner*—George R. Evanisko
*Attorney, Agent, or Firm*—John R. Merkling

[57] ABSTRACT

A cardiac stimulator lead and sleeve for anchoring the lead at its point of entry into a vein. More particularly, the present invention comprises a helical coil made of a resilient material that is capable of being uncoiled and wrapped around the lead and/or the vein such that it is biased to resume its fully coiled state and thereby frictionally engages the vein and or lead and functions as an anchoring device for the lead.

5 Claims, 3 Drawing Sheets

FIG. 1
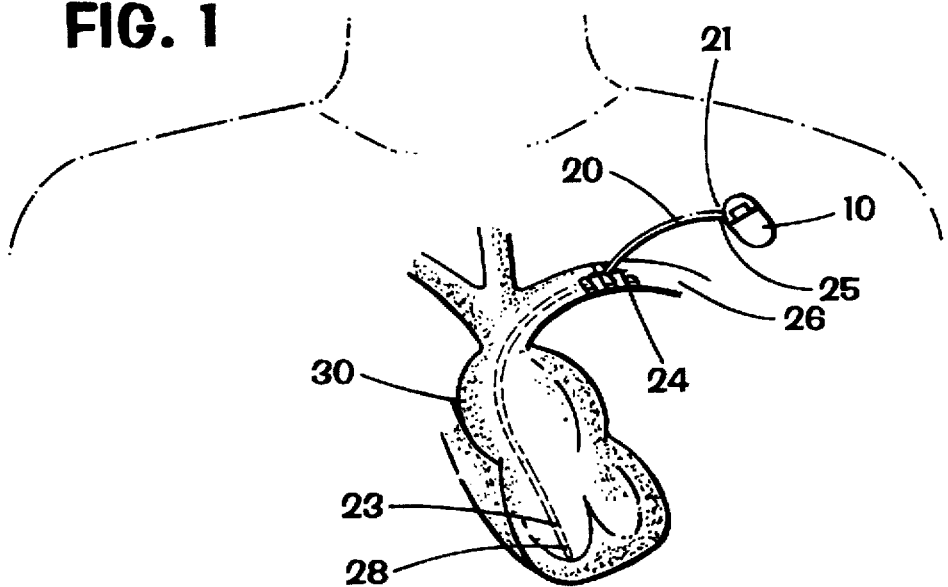
FIG. 2
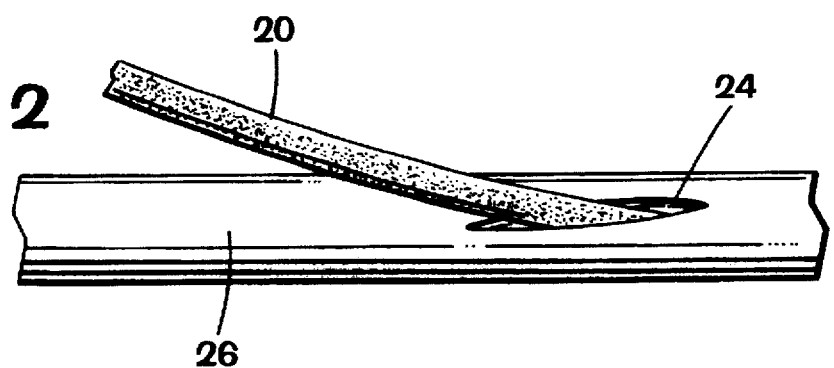
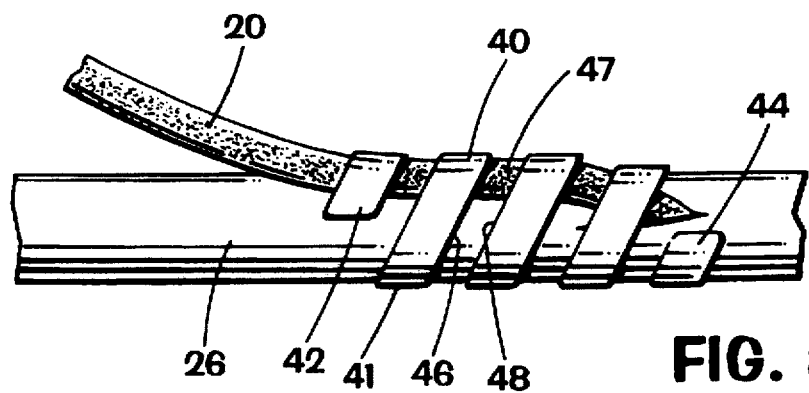
FIG. 3

SELF-CLAMPING ANCHORING SLEEVE

TECHNICAL FIELD OF THE INVENTION

The present invention relates to the field of implantable medical devices and more particularly to suture sleeves for implantable leads, catheters and the like. Still more particularly, the present invention relates to a cardiac stimulator lead system having a suture collar or sleeve that is received around a lead for fixing the lead to a vein into which the lead is inserted or to surrounding tissue.

BACKGROUND OF THE INVENTION

A normal human heart contains a natural pacemaker by which rhythmic electrical excitation is developed. If the body's pacemaker performs correctly, blood is oxygenated in the lungs and efficiently pumped by the heart to the body's oxygen-demanding tissues. Various factors affect the human heart rate and contribute to changes of rate from what is termed the normal sinus rate range (rates generally ranging in adults from 60 to 100 beats per minute). In healthy persons, tachycardia (100 to 160 beats per minute) is experienced as a result of such things as physical or emotional stress (exercise or excitement), consumption of alcoholic or caffeinated beverages, cigarette smoking, or ingestion of certain drugs. Variation from normal sinus rate range is generally characterized as cardiac arrhythmia, and arrhythmia rates exceeding the upper end of the sinus rate range are termed tachyarrhythmias. Arrhythmia rates below the normal sinus rate range are termed bradycardia.

Arrhythmias typically arise in the atria or ventricles as a consequence of an impairment of the heart's electrical electro-physiologic properties such as excitability, conductivity, and automaticity (rhythmicity). Such arrhythmias require special treatment. Cardiac pacemakers, chronically implanted within the patient's body, and connected to the heart by one or more leads, are frequently used to control bradycardia conditions. Implantable cardioverter-defibrillators, also implanted chronically in the patient's body and connected to the heart by one or more leads, can be used to control tachyarrhythmias, life-threatening or not, and life-threatening fibrillations.

A pacemaker (or "pacer" as it is commonly labeled) is an implantable medical device that delivers electrical pulses to an electrode implanted adjacent the patient's heart in order to stimulate the heart so that it will beat at a desired rate. An in-depth explanation of certain cardiac physiology and pacemaker theory of operation is provided in U.S. Pat. No. 4,830,006. Pacers and other implantable electrical stimulation devices generally comprise a power source and at least one lead extending from the power source to the point of stimulation. An implanted lead must be capable of conforming to the body in which it is implanted. In addition, implanted leads are subject to repeated flexing due to heartbeat, breathing or other body movements. Pacing leads, which extend into and sometimes through the heart itself are particularly subject to rigorous and continuous flexing. Improvements in pacemaker technology have increased the life of the devices and thus increased the period for which a lead is expected to operate without failure. It has been estimated that, in a 10-year period, a pacemaker lead must withstand over 360,000,000 flexes. For these reasons, highly advanced leads have been developed that are highly flexible, resilient and conductive. In general, implantable leads are fragile and susceptible to mechanical damage that reduces their useful lives.

There are generally two techniques for implanting leads used to conduct electrical signals to the heart. The first technique requires surgery to expose the myocardial tissue, whereby an electrode is affixed to the epicardial tissue. In the second technique the lead is inserted through a body vessel, such as a vein, into the heart, where an electrode contacts the endocardiac tissue. In the latter technique, the endocardial lead is often secured to the heart through the endothelial lining by a helix affixed to a distal end of the lead. When the end of the lead contacts the lining of the heart at a desired location, the lead may be secured in place by rotating the lead and screwing the helix into the heart tissue. Other types of active or passive fixation have also been used to secure the lead to the inner wall of the heart, such as hooks or tines.

It is generally deemed desirable to secure an implantable lead at an additional point along its length, so that movement of the lead from its desired position is minimized. This is typically accomplished by providing means to fix the position of the lead at the point where it enters a ligated vein. In the past, various techniques and mechanisms have been proposed for securing implanted or partially implanted leads to a vein. For example, an early type of securing means comprised a butterfly type anchoring sleeve that was attached to the lead body during implantation. The wings of the butterfly type sleeve provided a structure adapted to be sutured to a vein or underlying tissue and further protected the lead insulation from the stress of having a suture tied around it directly.

Another type of lead protection and attachment can be provided in the form of a silicone rubber sleeve that is pre-fitted around the lead during the manufacturing process. In operation the physician slides the sleeve to the point where the lead enters the vein and then secures the sleeve to the vein or underlying tissue. Sleeves of this type are often tightened or secured around the vein by means of ligatures, which may rest in guide grooves that encircle the sleeve. Additional examples of devices adapted to protect a lead at the point where it enters a vein are disclosed in U.S. Pat. Nos. 5,273,053, 4,516,584 and 5,129,405.

A common problem with prior art sleeves is that each sleeve is sized to receive only a particular size of lead. Therefore, a large inventory of sleeves must be maintained in order to accommodate the various lead sizes. Moreover, inherent tolerances affecting the fit between the lead and the sleeve must be considered. If the wrong size sleeve is used, the lead may not be adequately affixed to the vein and slippage may occur.

Another problem common among prior art suture sleeves is that ligatures are typically required to tighten the sleeve around the vein and lead. The application of ligatures is an additional step that increases the length of the surgical procedure. In addition, ligatures may become tangled or break, adding another category of possible failure to the risks associated with the lead implantation process.

Thus, it is desirable to provide a method and apparatus for affixing an implantable lead to a vein that avoids the problems and risks associated with the use of prior art suture sleeves.

SUMMARY OF THE INVENTION

The present invention comprises a helical strip of resilient, biocompatible material that can be wound around an implantable lead and/or a vein or body tissue adjacent to the point where the lead enters the vein.

BRIEF DESCRIPTION OF THE DRAWINGS

Other objects and advantages of the invention will become apparent upon reading the following detailed description and upon reference to the accompany drawing in which:

FIG. 1 is a fragmentary view of a chest showing a pacer and lead extending therefrom into a heart;

FIG. 2 is an enlarged view of a entering a vein through an incision;

FIG. 3 is an enlarged perspective view of a first embodiment of the sleeve of the present invention surrounding an implantable lead at its point of entry into a vein;

DETAILED DESCRIPTION OF THE PREFERRED EMBODIMENT

Figure 4:
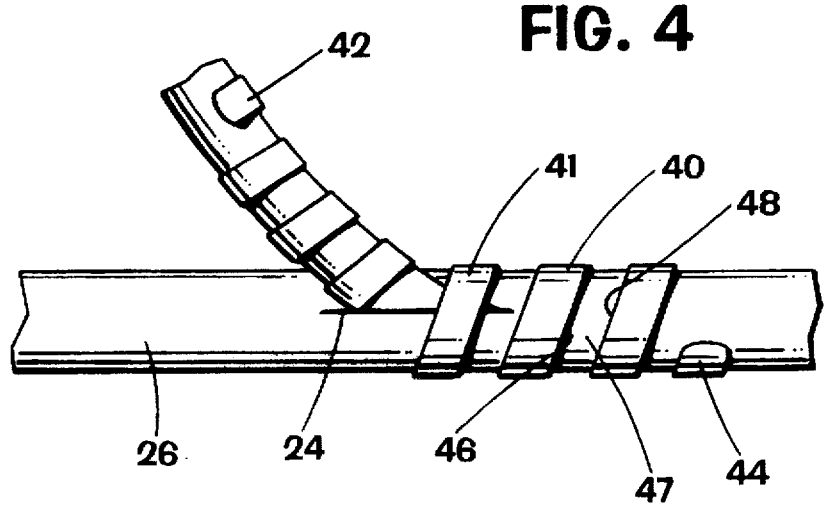
FIG. 4 is an enlarged perspective view of a first alternative method of using the sleeve of the present invention to anchor an implantable lead at its point of entry into a vein.

As shown in FIG. 1, a preferred embodiment of my invention comprises a lead system for a cardiac stimulator 10. The lead system comprises a lead 20 having a proximal end 21 and a distal end 23. An electrode 28 at the distal end 23 is in electrical communication with a plug 25 at the proximal end 21. Preferably, the plug 25 is a standard configuration, such as a VS-1 configuration which is well known in the art. As best shown in FIG. 2, lead 20 is substantially aligned with vein 26 at the point where it passes through opening 24. Once lead electrode 28 is affixed to the endocardial tissue of the heart 30, it is desirable to anchor the body of lead 20 at least one additional point, so as to prevent lead 20 from pulling out of or away from vein 26.

Referring now to FIG. 3, a first embodiment of the self-clamping sleeve of the present invention comprises a helix 40 having first and second ends 42, 44, respectively. It is preferred that the ends 42, 44 be rounded, so as to reduce the risk of puncturing or otherwise damaging the body tissue or the lead itself. Helix 40 preferably comprises a substantially flat ribbon 41 of resilient material, such as polyurethane or silicone rubber that has been coiled into a helix. In some instances, it may be desirable to incorporate a metallic spine in the material that comprises ribbon 41. The resilient material preferably has a high plastic yield point, so that when helix 40 is uncoiled from its unbiased coiled shape, it is strongly biased to resume its coiled shape. When released, the helix 40 will resume its coiled shape without deformation.

As shown in FIG. 3, ribbon 41 includes first and second long edges 46, 48 respectively, which lie adjacent each other when helix 40 is in its unbiased state. A helical gap 47 is defined between edges 46, 48. Helix 40 can be constructed so that gap 47 is substantially closed and edges 46, 48 contact each other in the unbiased state, or can be constructed with a greater pitch, so that edges 46, 48 lie apart from each other, as shown. The embodiment shown in the Figure is not necessarily preferred and has been used for illustration purposes only.

Still referring to FIG. 3, helix 40 is used to hold lead 20 adjacent and parallel to vein 26 over a portion of its length at the point where lead 20 enters vein 26. When it is desired to install the present sleeve, helix 40 is uncoiled manually or mechanically, placed adjacent the vein in the region to which it is to be applied and then allowed to incrementally resume its unbiased, coiled shape as it is wrapped around the vein and lead. Because operation of the coil for its desired purpose depends on its frictional engagement with lead 20 and vein 26, it is preferred that helix 40 not be allowed to completely return to its unbiased state when it is installed. In order to ensure that helix 40 does not fully resume its unbiased state even when deployed on very small veins and leads, it is preferred that the inside diameter of helix 40 be approximately 1 mm. Because it is flexible, a helix 40 having a single inside diameter can be used around leads and veins having a range of diameters. Alternatively, helix 40 can be provided in different sizes, although it is preferred that the inside diameter of the unbiased coil be at least slightly less than the outside diameter of the vein around which it is to be placed.

In the embodiment shown in FIG. 3, most of the body of lead 20 lies upstream of opening 24. Helix 40 wraps around lead 20 and vein 26 in a manner that holds them parallel and adjacent. Referring now to FIG. 4, an alternative technique for using the present sleeve is shown. Namely, a portion of helix 40 adjacent end 44 is wrapped around vein 26 below the point where lead 20 is inserted and a second portion of helix 40, adjacent end 42, is wrapped around lead 20 only. As in FIG. 3, the embodiment in FIG. 4 relies on frictional engagement with lead 20 and vein 26 to prevent movement of lead 20 relative to vein 26.

Figure 5A:
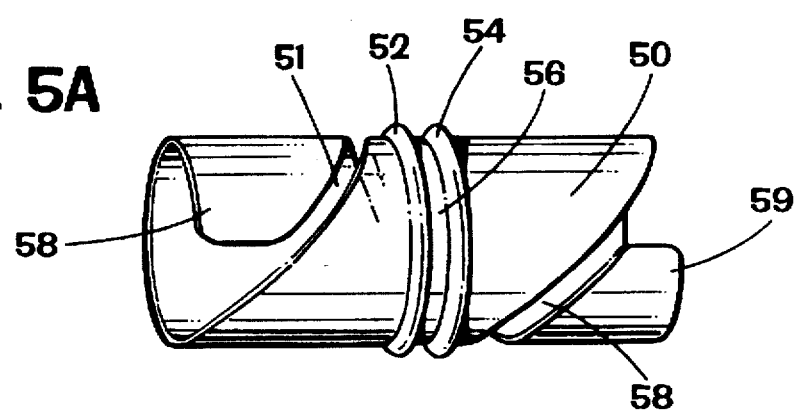
FIGS. 5A and 5B are perspective views of opposite sides of an alternative embodiment of the sleeve of the present invention, which is adapted to be used in conjunction with ligatures.
Figure 5B:
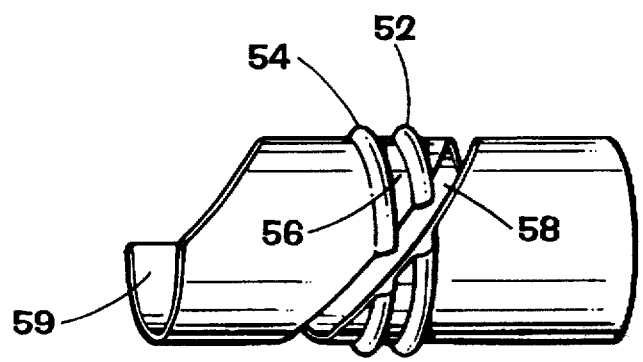

Referring now to FIGS. 5A and 5B, it may be desired to provide a sleeve 50 constructed according to the principles of the present invention with means for accommodating ligatures. One way to accomplish this is to provide a pair of parallel circumferential ridges 52, 54 on the outside of sleeve 50. Ridges 52, 54 define a groove 56 therebetween. Alternatively, a circumferential groove can be provided directly in the surface of the sleeve 50 and ridges 52, 54 can be omitted, although the depth of the groove in this instance would be limited by the thickness of the material. After grooved sleeve 50 is wrapped around the vein and/or lead at the desired point, a conventional ligature (not shown) is tied around sleeve 50 and retained in groove 56. In this manner, the ligature can be used to tighten sleeve 50 around the vein 26 and/or lead 20 without slipping from its desired position on the sleeve 50. As shown in FIG. 5B, as circumferential ridges 52, 54 encircle sleeve 50, they align on opposite sides of the helical gap 58 that is defined between the long edges of the material. Gap 58 has no significant effect on operation of the ligature.

The circumferential grooves shown in FIGS. 5A and 5B can be applied to a sleeve of any length. A single sleeve 50 can be provided with a plurality of grooves, such as in the case of longer sleeves, where it is desired to provide tightening sutures at more than one location. In addition, the grooves themselves can be provided in any suitable geometry that facilitates use of ligatures on the sleeve.

According to a particular embodiment illustrated in FIGS. 5A–B, a sleeve according to the present invention can be manufactured using a conventional suture sleeve as the base structure. Specifically, a conventional molded suture sleeve comprising an elongate body having a lumen therethrough can be provided with a helical slit extending the length of the body. If desired, the corners that would otherwise be present at ends 58, 59 can be rounded as shown, so as to reduce the risk of tissue damage. In this manner, a helical sleeve 50 is formed from a preexisting suture sleeve and the radius of the lumen can then easily be increased by rotating the ends 58, 59 relative to one another. This technique allows suture sleeves that would otherwise be limited to use on a very narrow range of lead sizes to be used on a much larger range of sizes, thereby reducing cost and inventory. In addition the helical gap created in this manner is preferable to a longitudinal slit because it reduces the risk of pinching the underlying lead insulation.

According to an alternative manufacturing technique, the present sleeve could also be manufactured and shipped in long coils. The long coils could then be custom cut to the desired length just prior to the time of implantation. This would allow certain advantages in manufacturing and inventorying and would allow the surgeon to optimize the sleeve length for each implantation.

Figure 6:
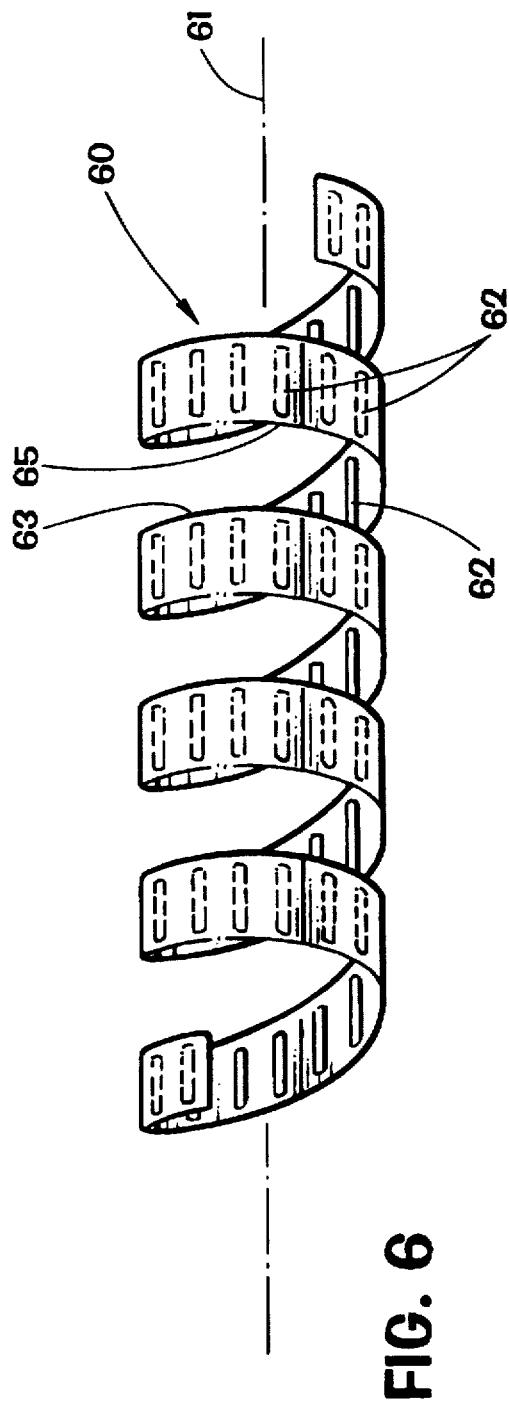
FIGS. 6 and 7 are perspective views of additional variations on the sleeve shown in FIG. 3.
Figure 7:
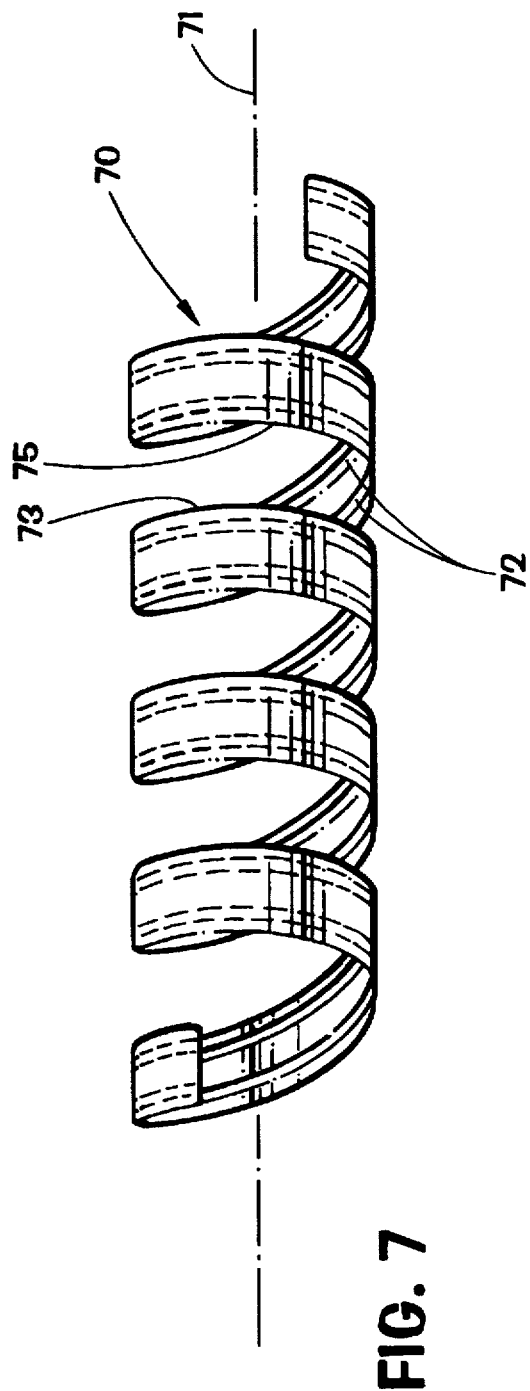

Referring now to FIG. 6, an alternative embodiment 60 of the present coil sleeve includes a plurality of ridges 62 extending generally transversely between long edges 63, 65. As shown in FIG. 6, ridges 62 can be positioned so that they lie substantially parallel to the coil axis 61. Similarly, in FIG. 7 another alternative embodiment 70 of the present coil sleeve includes a plurality of ridges 72 extending generally parallel to long edges 73, 75. The purpose of ridges 62 and 72 is to enhance frictional engagement of the coil sleeve 60, 70 with the object around which it is wrapped. Thus, it will be understood that ridges 62, 72 can be reoriented and other suitable surface features, such as dimples, can be substituted for the ridges 62, 72 shown, without departing from the scope of the invention.

While preferred embodiments of this invention have been shown and described, modifications thereof can be made by one skilled in the art without the departing from the spirit or teaching of this invention. The embodiments described herein are exemplary only and are not limiting. Many variations and modifications of the system and apparatus are possible and are within the scope of the invention. Accordingly, the scope of the protection is not limited to the embodiments described herein, but is only limited by the claims which follow, the scope of which shall include all equivalence of the subject matter of the claims.

What is claimed is:

1. A method for anchoring an implantable lead to a blood vessel, comprising the steps of:
   (a) providing a lead, said lead having a proximal end and a distal end, an electrode adjacent said distal end and a plug adjacent said proximal end, said electrode being in electrical communication with said plug;
   (b) inserting said distal end into said blood vessel at an anchoring point such that at least a distal portion of said lead lies within said blood vessel and a proximal portion lies outside said blood vessel;
   (c) providing a sleeve separate from said lead said sleeve comprising a resilient helix having an unbiased, coiled shape;
   (d) at least partially uncoiling the sleeve;
   (e) placing the uncoiled sleeve adjacent the blood vessel at the anchoring point; and
   (f) wrapping the sleeve around the blood vessel and lead while allowing the sleeve to partially resume its unbiased, coiled shape until it engages the lead and the blood vessel.

2. The method according to claim 1 further including the steps of the lead parallel and adjacent to the blood vessel and wrapping the coil around both the lead and the blood vessel in step (f).

3. The method according to claim 1, wherein step (f) comprises the steps of wrapping one end of the coil around the lead and another end of the coil around the blood vessel.

4. The method according to claim 1, further including the steps of providing at least one ligature and fastening said at least one ligature around the coil.

5. The method according to claim 1 wherein step (c) includes the steps of providing a relatively long length of coiled biocompatible resilient material and forming a coiled sleeve by cutting a desired length from the coiled material at time of implant.

* * * * *